(12) United States Patent
Mütze et al.

(10) Patent No.: US 8,955,917 B2
(45) Date of Patent: Feb. 17, 2015

(54) METHOD AND APPARATUS FOR INCREASING THE YIELD IN A DEPOSIT

(75) Inventors: Thomas Mütze, Freiberg (DE); Silke Röntzsch, Großröhrsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 103 days.

(21) Appl. No.: 13/702,605

(22) PCT Filed: Mar. 29, 2011

(86) PCT No.: PCT/EP2011/054769
§ 371 (c)(1),
(2), (4) Date: Dec. 7, 2012

(87) PCT Pub. No.: WO2011/154169
PCT Pub. Date: Dec. 15, 2011

(65) Prior Publication Data
US 2013/0076099 A1  Mar. 28, 2013

(30) Foreign Application Priority Data
Jun. 7, 2010 (EP) .................................... 10165037

(51) Int. Cl.
*E21C 39/00* (2006.01)
*E21B 44/02* (2006.01)
(Continued)

(52) U.S. Cl.
CPC ................. *E21B 44/02* (2013.01); *E21B 21/07* (2013.01); *E21B 49/005* (2013.01); *E21C 39/00* (2013.01); *G01N 15/0205* (2013.01); *G01N 2015/0019* (2013.01)
USPC .......................................................... 299/18

(58) Field of Classification Search
CPC .............................. E21C 39/00; G01N 37/005
USPC ........................ 299/7, 18; 73/152.02, 152.03
See application file for complete search history.

(56) References Cited

U.S. PATENT DOCUMENTS 2,082,329 A   6/1937   Foran et al. ...................... 175/48
2,167,393 A   7/1939   Muncy ............................. 175/49
(Continued)

FOREIGN PATENT DOCUMENTS

| CN | 1643233 A | 7/2005 | ............. E21B 21/08 |
| CN | 2919251 Y | 7/2007 | ............. G01N 15/00 |

(Continued)

OTHER PUBLICATIONS

International Search Report and Written Opinion, Application No. PCT/EP2011/054767, 13 pages, May 11, 2011.
(Continued)

*Primary Examiner* — David Bagnell
*Assistant Examiner* — Michael Goodwin
(74) *Attorney, Agent, or Firm* — King & Spalding L.L.P.

(57) ABSTRACT

A method for increasing the yield of a deposit including a rock which including at least one valuable mineral to be exposed by comminuting the rock and at least one further mineral, may include the following steps: performing a boring operation using a boring device prior to extracting the rock, determining at least one predetermined boring parameter for the boring device, determining at least one measured value characterizing a current boring behavior of the boring device, and performing a computational elimination of a dependency of the at least one measured value on the at least one boring parameter, wherein at least one rock texture-dependent characteristic value is obtained, and wherein the at least one characteristic value is used as a measure for a mineral particle size of the at least one valuable mineral in the rock and for setting an optimum degree of comminution when comminuting the rock.

16 Claims, 4 Drawing Sheets

(51) Int. Cl.
*E21B 21/07* (2006.01)
*E21B 49/00* (2006.01)
*G01N 15/02* (2006.01)
*G01N 15/00* (2006.01)

(56) References Cited

U.S. PATENT DOCUMENTS

| | | | | |
|---|---|---|---|---|
| 3,528,514 | A | 9/1970 | Sandvig | 175/49 |
| 3,645,131 | A | 2/1972 | Turner et al. | 73/152.04 |
| 3,887,020 | A | 6/1975 | Chaffin | 175/206 |
| 3,968,845 | A | 7/1976 | Chaffin | 175/60 |
| 4,098,698 | A | 7/1978 | Lamothe | 210/309 |
| 4,633,712 | A * | 1/1987 | Scieszka | 73/866 |
| 6,301,953 | B1 | 10/2001 | Zamfes | 73/38 |
| 6,453,727 | B1 | 9/2002 | Lenormand et al. | 73/38 |
| 6,904,981 | B2 | 6/2005 | Van Riet et al. | 175/66 |
| 7,980,329 | B2 | 7/2011 | Spiecker et al. | 175/206 |
| 8,042,753 | B2 | 10/2011 | Yamaguchi et al. | 241/101.74 |
| 8,240,480 | B2 | 8/2012 | Shaw et al. | 209/11 |
| 2003/0182997 | A1 | 10/2003 | Williams | 73/152.23 |
| 2005/0087018 | A1 | 4/2005 | Zamfes | 73/601 |
| 2006/0107772 | A1 | 5/2006 | Shinn, II et al. | 73/864.43 |
| 2007/0137293 | A1 | 6/2007 | Pop et al. | 73/152.23 |
| 2008/0202811 | A1* | 8/2008 | Zamfes | 175/46 |
| 2009/0302141 | A1* | 12/2009 | Yamaguchi et al. | 241/33 |
| 2010/0000055 | A1 | 1/2010 | Poulakis | 24/30.5 R |

FOREIGN PATENT DOCUMENTS

| | | | | |
|---|---|---|---|---|
| CN | 101395336 | A | 3/2009 | E21B 21/01 |
| CN | 101553323 | A | 10/2009 | B06C 5/342 |
| DE | 10008106 | A1 | 8/2001 | E21B 49/00 |
| DE | 10116363 | A1 | 10/2002 | E21B 47/00 |
| RU | 2268364 | C2 | 1/2006 | E21B 49/00 |
| WO | 2009/105469 | A2 | 8/2009 | E21B 43/34 |
| WO | 2010/000055 | A1 | 1/2010 | E21B 21/06 |
| WO | 2011/154168 | A1 | 12/2011 | E21B 21/06 |
| WO | 2011/154169 | A1 | 12/2011 | E21B 21/07 |
| WO | 2011/154170 | A1 | 12/2011 | E21B 21/06 |

OTHER PUBLICATIONS

International Search Report and Written Opinion, Application No. PCT/EP2011/054769, 13 pages, May 11, 2011.

International Search Report and Written Opinion, Application No. PCT/EP2011/054771, 24 pages, Jul. 4, 2011.

Holmes, Ralph J., "Correct Sampling and Measurement—the Foundation of Accurate Metallurgical Accounting," Chemometrics and Intelligent Laboratory Systems, vol. 74, Elsevier Science Publishers, 14 pages, Mar. 12, 2004.

Australian Office Action, Application No. 2011264086, 3 pages, Oct. 1, 2013.

Australian Office Action, Application No. 2011264084, 3 pages, Mar. 11, 2014.

Australian Office Action, Application No. 2011264085, 3 pages, Jun. 2, 2014.

Chinese Office Action, Application No. 2011800283838, 12 pages, Jun. 30, 2014.

Australian Office Action, Application No. 2011264085, 2 pages, Oct. 13, 2014.

* cited by examiner

METHOD AND APPARATUS FOR INCREASING THE YIELD IN A DEPOSIT

CROSS-REFERENCE TO RELATED APPLICATIONS

This application is a U.S. National Stage Application of International Application No. PCT/EP2011/054769 filed Mar. 29, 2011, which designates the United States of America, and claims priority to EP Patent Application No. 10165037.2 filed Jun. 7, 2010 The contents of which are hereby incorporated by reference in their entirety.

TECHNICAL FIELD

The disclosure relates to a method and an apparatus for increasing the yield in a deposit comprising a rock which comprises at least one valuable mineral which is to be exposed by comminution of the rock, and at least one further mineral.

BACKGROUND

In order to exploit a deposit efficiently the valuable mineral contained in the rock must be exposed and separated off as completely as possible. Different degrees of comminution of the rock are required for exposure of the valuable mineral depending on the mineral grain size thereof. A rock containing minerals having a high grain size must therefore be comminuted less to expose the valuable mineral than a rock containing minerals having a smaller grain size.

The "mineral grain size" of the valuable mineral is taken here to mean not the grain size of the crystallites of this mineral but the local spatial extent of the phase of valuable mineral in the rock.

Previously the extracted rock was comminuted to a mean mineral grain size, with a first part of the rock which comprises a valuable mineral having a high grain size being comminuted to an unnecessary extent, and a second part of the rock which comprises a valuable mineral having a smaller grain size being insufficiently comminuted. The unnecessarily intensive comminution of the first part of the rock leads to an unnecessarily high consumption of energy for the comminution process. By contrast, the insufficient comminution of the second part of the rock leads to inadequate exposure, and consequently to inadequate separability of the valuable mineral, and therefore to ineffective exploitation of the deposit.

The mineral grain size and distribution of minerals in a rock were previously determined in a time-consuming manner in that rock samples are taken at various sites in a deposit and analyzed. Approximately first-sized lumps of rock are collected in deposits for this purpose and/or exploration drilling operations are carried out in a coarse grid to obtain cores which can be evaluated. These rock samples are analyzed in the laboratory with respect to their mineralogical and chemical composition. While the chemical analysis substantially determines the type and extent of the elements present, the type and extent of the minerals present and their spatial arrangement is determined in the mineralogical analysis. The rock samples are partially ground in the direction of defined spatial axes in order to determine the spatial arrangement of the minerals. The spatial arrangement and distribution of the minerals in the rock may be discerned by way of an optical analysis of the thin or ground sections, under a microscope for example. A spatially widely distributed arrangement of the minerals is associated with a low grain size of the minerals, while agglomerations of minerals at certain locations are associated with a higher mineral grain size.

Only a small amount of information may thus be provided with respect to the structure of a deposit or the spatial mineral grain size distribution of the valuable mineral in the deposit, and this information can only be provided after a considerable delay.

Deposit modeling, i.e. creation of a model of the deposit comprising the three-dimensional recording of layers of rock or rock formations having different grain sizes of the valuable mineral, is possible only to a limited extent owing to the small amount of information available. Extraction and comminution of the rock geared toward the rock that is present locally, i.e. its valuable mineral content and the grain size thereof, is therefore possible only to a limited extent.

WO 2010/000055 A1 discloses a method and a device for, in particular continuous, on-site analysis of drilling cuttings from drilling mud. A sample of the drilling cuttings which is representative of the rock formation being drilled is taken and analyzed with respect to the type of rock and the chemical composition. Drilling parameters, comprising the drilling depth, gamma radiation emissions and/or additional parameters are optionally also logged and correlated with the results of the sample analysis.

SUMMARY

In one embodiment, a method is provided for increasing the yield in a deposit comprising a rock which comprises at least one valuable mineral which is to be exposed as a result of the rock being comminuted, and at least one further mineral, the method comprising: performing a drilling operation using a drilling tool prior to the rock being extracted, acquiring at least one predefined drilling parameter for the drilling tool, acquiring at least one measured value characterizing a current drilling behavior of the drilling tool, and performing a computational elimination of a dependency of the at least one measured value on the at least one drilling parameter, wherein at least one rock-texture-dependent characteristic value results, and wherein the at least one characteristic value is used as a measure for a grain size of the at least one valuable mineral in the rock and for the purpose of setting an optimum degree of comminution during comminution of the rock.

In a further embodiment, the at least one rock-texture-dependent characteristic value is compared with predetermined characteristic values for the rock to which a specific grain size of the at least one valuable mineral and an optimum degree of comminution is assigned in each case, wherein, in the case of a match of the at least one rock-texture-dependent characteristic value with one of the predetermined characteristic values, the grain size of the valuable mineral assigned thereto and the assigned optimum degree of comminution are also assigned to the at least one rock-texture-dependent characteristic value. In a further embodiment, an ore mineral is exposed as the valuable mineral by comminution of the rock. In a further embodiment, a depth of a drill bit of the drilling tool and/or position data concerning the position of the drilling tool in the deposit is acquired during the drilling operation and is logically linked to the measure, determined at this location, and wherein during extraction of the rock at this location the associated position-dependent measure is used for the purpose of setting the optimum degree of comminution for the extracted rock. In a further embodiment, the at least one drilling parameter is formed from a pressure of the drill bit of the drilling tool and/or a rotational speed of the drill bit and/or a gas volume flow of a gas stream for removing drillings at the drill bit and/or an impact frequency of the drill bit and/or a previous period of use of the drill bit and/or material or geometric data of the drill bit. In a further embodiment, the at least one measured value characterizing the current drilling behavior is chosen from the group of measured values comprising a drill speed, a resulting torque at the top drive of the drill bit, a gas pressure of the gas stream for removing drillings at the drill bit, an energy input into the drilling tool and a vibration behavior of a drill pipe of the drilling tool. In a further embodiment, the at least one rock-texture-dependent characteristic value is also used for controlling an extraction or blast operation and/or a conveying operation and/or a material management operation in the region of the deposit.

In another embodiment, an apparatus is provided for performing any of the methods disclosed above, the apparatus comprising: at least one comminution machine for comminuting the rock, wherein a degree of comminution of the rock can be changed, at least one control and/or regulating unit for setting the optimum degree of comminution at the at least one comminution machine, at least one drilling tool, at least one device for acquiring the at least one drilling parameter and the at least one measured value, and at least one computing unit for performing a computational elimination of a dependency of the at least one measured value on the at least one drilling parameter and for determining the at least one rock-texture-dependent characteristic value, and at least one transmission device for transmitting at least one manipulated variable, determined on the basis of the measure, to the at least one control and/or regulating unit for setting the optimum degree of comminution at the at least one comminution machine during comminution of the rock.

In a further embodiment, the at least one transmission device corresponds to the at least one computing unit. In a further embodiment, at least one device for acquiring the at least one measured value is present on the at least one drilling tool in the form of at least one structure-borne noise sensor for detecting a vibration behavior of the drill pipe of the drilling tool. In a further embodiment, the at least one computing unit is also configured to use the at least one rock-texture-dependent characteristic value for controlling an extraction or a blast operation and/or a conveying operation and/or a material management operation in the region of the deposit. In a further embodiment, the device also comprises an extraction tool for the rock. In a further embodiment, the drilling tool and/or the extraction tool comprise/comprises a GPS unit.

BRIEF DESCRIPTION OF THE DRAWINGS

Example embodiments will be explained in more detail below with reference to figures, in which.

DETAILED DESCRIPTION

Figure 1:
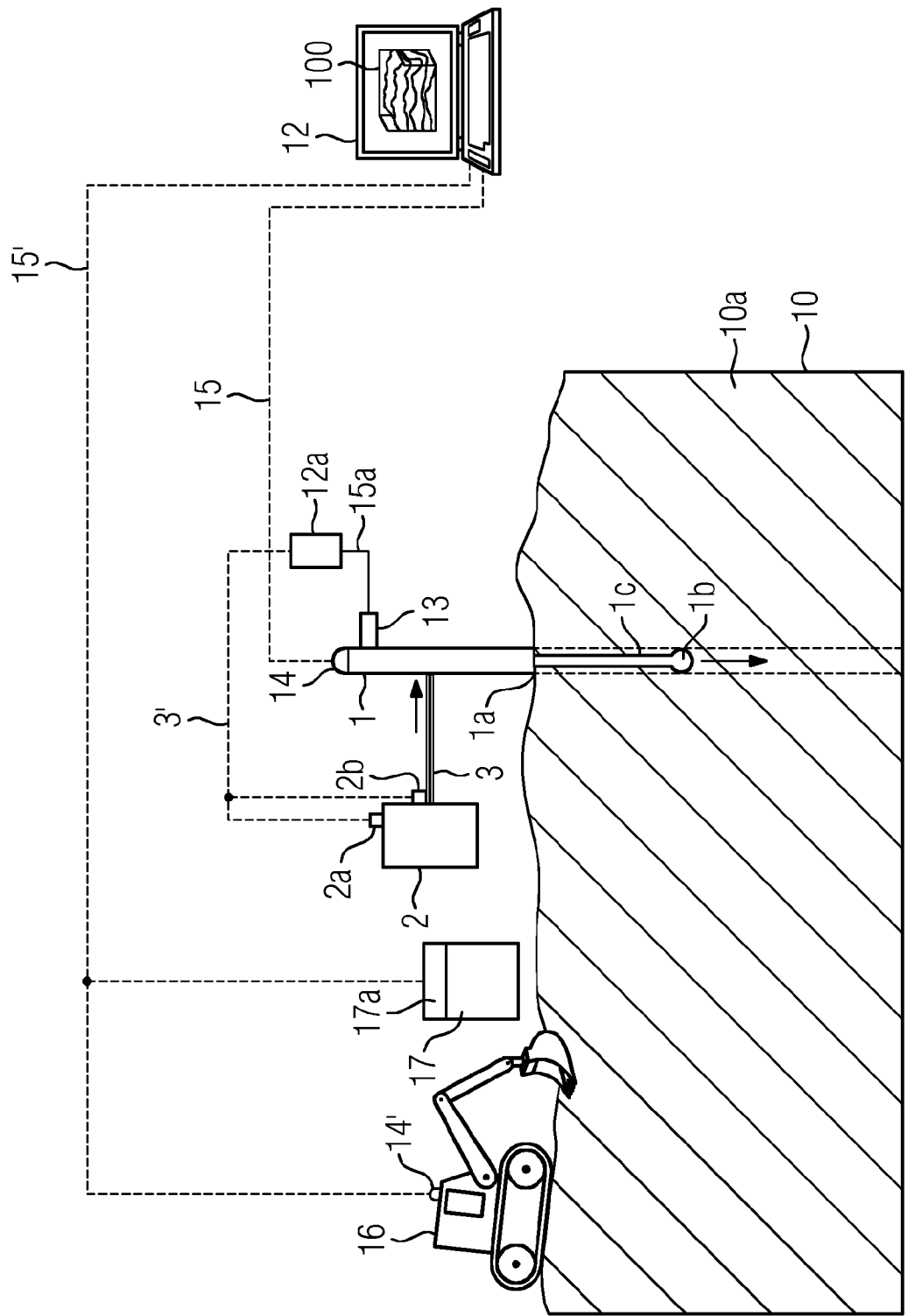
FIG. 1 schematically shows an apparatus for performing a method and a sequence of the method, FIG. 2 schematically shows a further apparatus for performing a method and a sequence of the method, FIG. 3 schematically shows a diagram of a deposit model, and FIG. 4 schematically shows the possible data and material flows for a method.

Embodiments of the present disclosure provide a method and an apparatus whereby a grain size of the at least one valuable mineral and an optimum degree of comminution assigned thereto can be determined for the rock in high resolution in order to increase the yield in a deposit.

Some embodiments provide a method for increasing the yield in a deposit comprising a rock which comprises at least one valuable mineral which is to be exposed as a result of the rock being comminuted, and at least one further mineral, comprising the following steps:

performing a drilling operation using a drilling tool prior to the rock being extracted, acquiring at least one predefined drilling parameter for the drilling tool, acquiring at least one measured value characterizing a current drilling behavior of the drilling tool, and performing a computational elimination of a dependency of the at least one measured value on the at least one drilling parameter, wherein at least one rock-texture-dependent characteristic value results, and wherein the at least one characteristic value is used as a measure for a grain size of the at least one valuable mineral in the rock and for the purpose of setting an optimum degree of comminution during comminution of the rock.

Other embodiments provide an apparatus for performing the disclosed method, comprising at least one comminution machine for comminuting the rock, wherein a degree of comminution of the rock can be changed, at least one control and/or regulating unit for setting the optimum degree of comminution at the at least one comminution machine, at least one drilling tool, at least one device for acquiring the at least one drilling parameter and the at least one measured value, and at least one computing unit for performing a computational elimination of a dependency of the at least one measured value on the at least one drilling parameter and for determining the at least one rock-texture-dependent characteristic value, and at least one transmission device for transmitting at least one manipulated variable, determined on the basis of the measure, to the at least one control and/or regulating unit for setting the optimum degree of comminution at the at least one comminution machine during comminution of the rock.

Certain embodiments use the knowledge that the measured values, characterizing a current drilling behavior of the drilling tool, which can be acquired during a drilling operation depend not only on the drilling parameters but also have a direct correlation with the grain size of the at least one valuable mineral which is present in the rock which has been drilled through. Targeted evaluation of the measured values, following computational elimination of their dependency on the drilling parameters, surprisingly enables sufficiently accurate conclusions to be drawn about the grain sizes present in the rock which has been drilled through and the creation of a deposit model. Targeted extraction and comminution matched to the locally present mineral grain size are possible with the aid of the model, so the valuable mineral present is always optimally exposed. Particularly effective exploitation of the deposit and cost-efficient extraction operation result.

Thus, for example, the drilling speed is dependent inter alia on the strength and composition of the rock which has been drilled through, high strength and/or an accumulation of hard minerals leading to a reduction in the drilling speed. However, the drilling speed is also dependent on which drilling tool and drilling device is used. The type, geometry and state of wear of the drill bit are important in particular here. These drilling parameters are obviously to be taken into account when assessing the drilling speed.

The computational elimination of the dependency on the drilling parameters requires a manageable number of preliminary tests in which the individual influencing variables are determined and correlated with one another. The database created in this way may be stored on the at least one computing unit and is used to determine the characteristic value dependent solely on the texture of the rock.

With knowledge of the characteristic value, dependent on the rock structure, which forms a measure for the grain size of the valuable mineral and is used to create a deposit model, fast and uncomplicated determination and assignment of the degree of comminution that is optimum for the rock which has been drilled through is possible.

An optimum degree of comminution is regarded as a degree of comminution for the respective rock at which comminution is carried out up to exposure of the at least one valuable mineral present, but not beyond.

The method and the apparatus allow particularly fast and sufficiently accurate adjustment of the degree of comminution to the locally present grain size of the valuable mineral in the rock. The characteristic value dependent on the rock texture is assigned to a mineral grain size and consequently to an optimum degree of comminution for the rock which has been drilled through during the drilling operation, such that the data for each drill hole is available on a depth-dependent and timely basis.

Instead of evaluation of the cores obtained during core drilling operations to determine the respective rock structure, the drilling behavior of a drilling tool can now simply be analyzed when investigating a deposit. The number of drill holes can be significantly increased since complex laboratory analyses of cores are no longer required. In particular drilling operations to provide blast holes for determining the respective rock structure can now also be used, and these are placed in a narrower grid than for exploration drillings. Blast holes are typically sunk at a horizontal distance of 2 to 5 m, it being possible to provide data with a vertical resolution in the dm range. Particularly fast and accurate deposit modeling, and consequently particularly efficient extraction of the deposit, is thus possible.

It has proven expedient if the at least one rock-texture-dependent characteristic value is compared with predetermined characteristic values for the rock, to which a specific grain size of the at least one valuable mineral and an optimum degree of comminution is assigned in each case, wherein, in the case of a match of the at least one rock-texture-dependent characteristic value with one of the predetermined characteristic values, the grain size of the valuable mineral assigned thereto and the assigned optimum degree of comminution are also assigned to the at least one rock-texture-dependent characteristic value. The creation of the database for this comparison requires a manageable number of preliminary tests for the respective drilling tool and the respective type of rock in order to determine the correlation between the drilling behavior of the drilling tool and the rock which has been drilled through.

An ore mineral may be exposed as the valuable mineral by comminution of the rock. "Ores" are designated as naturally occurring mineral aggregates of economic interest from which one or more reusable materials can be extracted by machining. In most cases these are minerals which to a greater or lesser extent contain metal components, such as iron, copper, nickel, tin, zinc, silver, gold, etc.

It may be advantageous if a depth of a drill bit of the drilling tool and/or position data concerning the position of the drilling tool in the deposit are acquired during the drilling operation and are logically linked to the measure, determined at this location, and that the associated position-dependent measure for setting an optimum degree of comminution of the extracted rock is used during extraction of the rock at this location. Extremely accurate deposit modeling, as has been explained already, is possible with knowledge of the characteristic values, present in all three dimensions of the deposit, which represent the grain size distribution of the at least one valuable mineral in the deposit. To determine the current position of the drilling tool during a drilling operation in the deposit as accurately as possible, the gradient of the drill hole in particular is measured and the position of the drilling starting point is acquired, e.g., using at least one GPS unit.

The apparatus may also comprise an extraction tool for extracting the rock and/or for conveying rock which has already been coarsely pre-comminuted in a blast, which tool also comprises at least one GPS unit.

The position data of an extraction tool is transmitted in particular using a wireless data transmission to the at least one computing unit. The extraction tool for extracting the rock can be formed by a discontinuous excavator, in particular a shovel or flat excavator, or a continuous excavator, such as a bucket wheel excavator or chain-and-bucket excavator, or the like. An extraction tool for conveying rock which has already been coarsely pre-comminuted using a blast can be formed by a wheel loader.

The liberated or dislodged rock is conventionally managed by way of a material supply system in which the position or storage location of the blasted or extracted rock is stored and by way of which the wheel loader can be controlled. The extracted or blasted rock is, optionally after intermediate storage, given up to dump trucks or conveyor belts and conveyed to the at least one comminution machine or conveyed directly into the at least one comminution machine, where further comminution of the rock is carried out until the valuable mineral is exposed.

The at least one drilling parameter is formed for example from a pressure of the drill bit of the drilling tool, and/or a rotational speed of the drill bit, and/or a gas volume flow of a gas stream for removing drillings at the drill bit and/or an impact frequency of the drill bit and/or a previous period of use of the drill bit and/or material or geometric data of the drill bit, and the like. The impact frequency is yielded inter alia from pressure and gas stream data.

The at least one measured value characterizing the current drilling behavior is chosen in particular from the group of measured values comprising a drilling speed, a resulting torque at the top drive of the drill bit, a gas pressure of the gas stream for removing drillings at the drill bit, an energy input into the drilling tool, vibration behavior of a drill pipe in the drilling tool, and the like.

At least one device is used for acquiring the at least one drilling parameter and/or the at least one measured value, characterizing the current drilling behavior of the drilling tool, it being possible to use sensors already present on the drilling tool or additional sensors attached to the drilling tool.

In one embodiment of the apparatus there is present on the at least one drilling tool at least one device in the form of at least one structure-borne noise sensor for acquiring a measured value, characterizing the current drilling behavior, in the form of a vibration behavior of the drill pipe of the drilling tool. It has been found that the properties of the rock which is currently being drilled through may be easily inferred from the vibration of the drill pipe, taking account of the drilling parameters.

FIG. 1 schematically shows an apparatus for performing a method in the region of a deposit 10 having rock 10a shown in section. The apparatus comprises a drilling tool 1 having a drill bit 1b and a drill pipe 1c in the region of a drilling starting point 1a and a unit 2 for providing a gas stream which receives drillings produced at the drill bit 1b and removes them in the direction of the earth's surface. The unit 2 is connected for this purpose by way of at least one gas line 3 to the drilling tool 1. A device 2a in the form of a gas volume flow sensor, which is used to acquire a drilling parameter in the form of the gas volume flow of the gas stream, is located on the unit 2. A further device 2b in the form of a gas pressure sensor for acquiring a measured value, characterizing the drilling behavior, in the form of the gas pressure of the gas stream is also located on the unit 2. Both the drilling parameter and the measured value are transmitted to a computing unit 12 which is arranged outside of the drilling operations. Whereas the drilling parameters are conventionally passed by the operator and/or various apparatuses to the computing unit 12, the measured values may be transmitted via radio 15 to the computing unit 12.

The drilling tool 1 has a GPS unit 14 in order to be able to identify the drilling position of the drilling tool 1 at the drilling starting point 1a in the deposit 10. The position data, in particular the current depth of the drill bit 1b and the drill hole gradient, is transmitted to the computing unit in particular via radio 15.

A structure-borne noise sensor 13 may also be installed on the drilling tool 1 and this is used for acquiring a measured value, characterizing the current drilling behavior, in this case the vibration behavior of the drill pipe 1c of the drilling tool 1. With knowledge of the drilling parameters predefined on the drilling tool 1 and the vibration behavior of the drill pipe 1c, a dependency of the vibration behavior on the drilling parameters can be computationally eliminated using a further computing unit 12a which is arranged in the vicinity of the drilling tool 1. The data concerning the vibration behavior is so extensive that a data transmission thereof via radio to the computing unit 12 may only be achieved with difficulty. However, an evaluation of the vibration data, made in the further computing unit 12a installed locally, can be transmitted via radio from the further computing unit 12a to the remotely arranged computing unit 12.

According to FIG. 1 the apparatus also comprises an extraction tool 16 for directly extracting the accumulated rock 10a, which tool likewise has a GPS unit 14'. The position data of the extraction tool 16 is transmitted in particular using a data transmission 15" via radio to the computing unit 12. The extraction tool 16 is in this case formed either by a discontinuous excavator, in particular a shovel or flat excavator, or by a continuous excavator, such as a bucket wheel excavator or chain-and-bucket excavator, or the like.

The extraction tool 16 passes the locally extracted rock 10a indirectly, for example following temporary storage monitored by way of a material management system, or directly to a comminution machine 17 which comprises a control and/or regulating unit 17a for setting the optimum degree of comminution.

Figure 2:
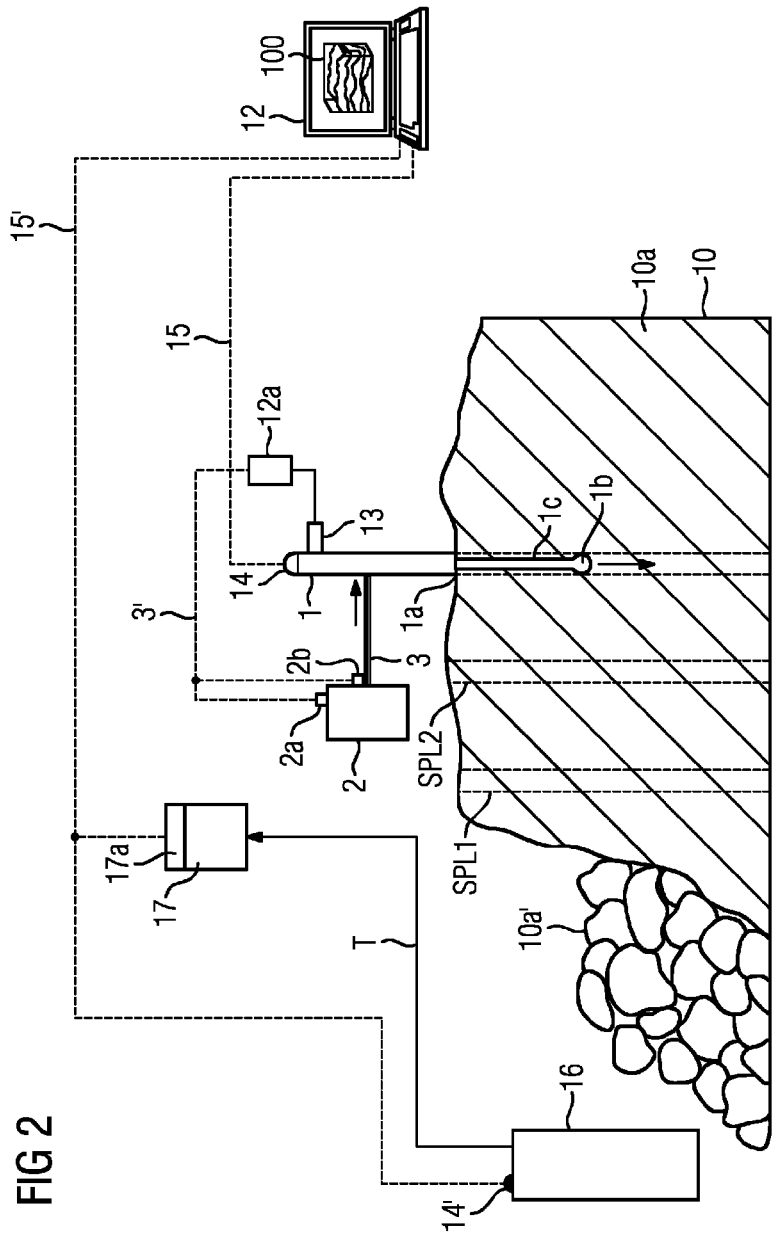

FIG. 2 schematically shows a further apparatus for performing a method in the region of a deposit 10 having rock 10a shown in section. Reference numerals identical to those in FIG. 1 denote identical elements.

In contrast to FIG. 1, the rock 10a is in this case provided with blast holes SPL1, SPL2 which the drilling tool 1 has formed. A number of blast holes may be introduced in the rock 10a at a horizontal distance of 2 to 5 m. The rock 10a is liberated from the accumulated rock 10a using a blast, the coarsely precomminuted rock 10a' then being received by an extraction tool 16, for example in the form of a wheel loader. Having been recorded by way of a material management system, and therefore retrievable again, it can now be temporarily stored or be conveyed directly to the comminution machine 17 (see arrow T).

According to the extraction site of the rock 10a, which is known to the computing unit 12 owing to the GPS unit 14' on the extraction tool 16, a manipulated variable is transmitted to the comminution machine 17 or its control and/or regulating unit 17a, in particular using a data transmission 15" via radio, as a function of the optimum degree of comminution previously determined for this extraction site and the extraction depth. This can also be performed automatically using the computing unit 12 or of course also on site by an operator.

The optimum degree of comminution is specified by the computing unit 12 according to the rock-texture-dependent characteristic value in such a way that the valuable mineral locally present in the rock 10a is optimally exposed. The comminution machine 17 now comminutes the rock following appropriate, in particular automatic, setting of its comminution tool in accordance with the optimum degree of comminution predefined in each case. Almost complete separation of the exposed valuable mineral from the further mineral can now take place, with the result that efficient exploitation of the deposit 10 is realized.

The computing unit 12 is used to perform computational elimination of a dependency of the at least one measured value on the at least one drilling parameter and to determine the at least one rock-texture-dependent characteristic value as a measure for setting an optimum degree of comminution of the rock 10a. In particular the computing unit 12 also corresponds in this case to the transmission device for transmitting at least one manipulated variable, determined on the basis of the measure, to the at least one control/regulating unit 17a for setting the optimum degree of comminution at the least one comminution machine 17. However, the transmission device can also be present separately from the computing unit 12 and be manually supplied with the data for the manipulated variable by the operator. The comminution machine 17 is controlled and/or regulated accordingly during extraction of the rock 10a at a certain drilling position or, as the case may be, removal of extracted rock 10a' from the deposit 10 or from a temporary storage facility.

With knowledge of the drilling parameters predefined at the drilling tool 1 and, for example, the vibration behavior of the drill pipe 1c, a dependency of the vibration behavior on the drilling parameters can be computationally eliminated using the computing unit 12. The result yielded is a rock-texture-dependent characteristic value, which is used as a measure for determining the optimum degree of comminution for this rock.

Figure 3:
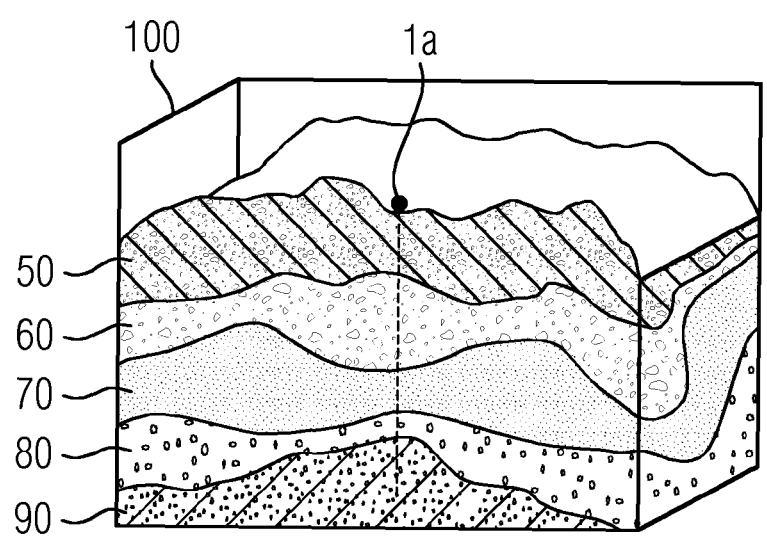

A deposit model 100 from which the distribution of the mineral phases in the deposit will be apparent can also be created using the computing unit 12 (see FIG. 3).

A deposit model 100 can be created on the basis of the determined mineral grain sizes of the valuable mineral at the various drilling sites in the deposit 10, and in particular also at different depths of the drill bit in the rock, with an appropriately high number of drilling sites or blast holes, and this model reproduces a sufficiently accurate three-dimensional image of the deposit 10. The spatial position 50, 60, 70, 80, 90 of rock having different local grain sizes of the valuable mineral can be seen in the deposit model 100. Five rock layers, located at different depths, having valuable minerals with different grain sizes, were determined proceeding from the drilling starting point 1a.

Figure 4:
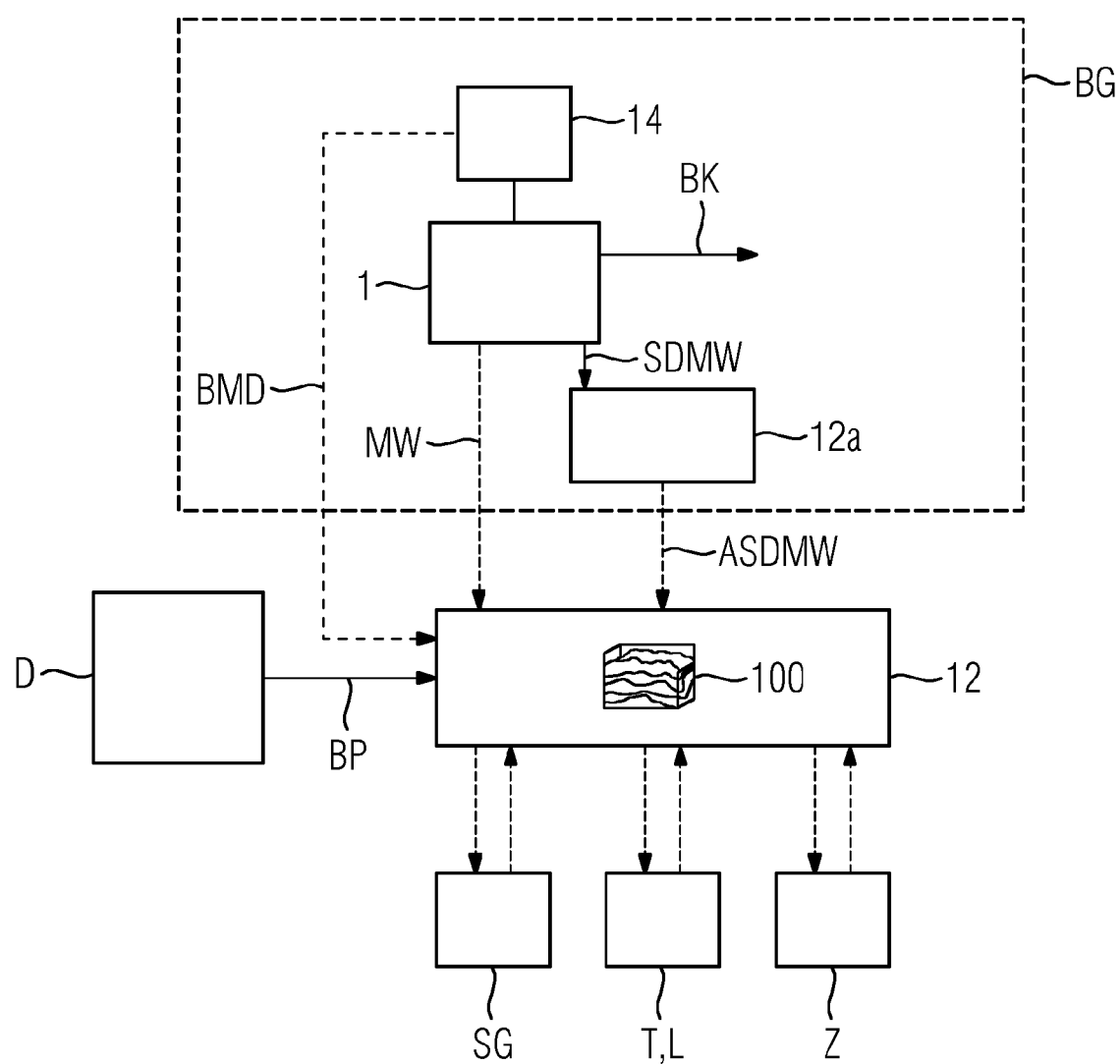

FIG. 4 schematically shows data and material flows for a possible method. The computing unit 12 is supplied via a data source D with the (typically known) drilling parameters BP, it being possible for the operator and/or other electronic equipment to be used as the data source. Drilling parameters BP in the form of data concerning the type of drilling tool 1, the type and geometry of the drill bit of drilling tool 1, the period of use during which the drill bit has already been operating, the pressure and/or rotational speed of the drill bit, etc. are transmitted. As a rule a wired data line is used here. During the drilling operation current measured values MW characterizing the drilling behavior are transmitted to the computing unit 12 by the drilling tool 1 or measured value sensors present thereon. The measured values MW are for example a drilling speed, an energy input into the drilling tool 1, etc. The current position data BMD of the drilling tool 1, in particular the drill bit, is also transmitted to the computing unit 12 by the GPS unit 14.

Once the measured values MW and position data BMD have been recorded in the region of the drilling operation BG, these are transmitted, e.g., wirelessly (see broken lines), to the computing unit 12 which is arranged spatially separately therefrom.

Measured values MW relating to the drilling behavior, which are present in the form of vibration data SDMW, are evaluated in the further computing unit 12a directly in the region of the drilling operations BG and the evaluation is then transmitted wirelessly to the computing unit 12.

The entire extraction operation in the region of the deposit 10 may be controlled on the basis of the model 100 determined in the computing unit 12, primarily with respect to an extraction or a blast SG, as well as conveying T, storage L and rock comminution Z of the extracted rock. Thus, with knowledge of the model 100, and optionally the local strength of the rock, the locally used quantity of explosive for example can be adjusted, the extracted rock stored at different locations according to property, wherein rock having in particular the same grain size of the valuable mineral is combined, conveyed in the desired sequence to the comminution machine and comminuted there to different degrees as a function of the grain size of the valuable mineral.

The figures merely illustrate one example of the apparatus and method. The person skilled in the art is easily capable of adapting the disclosed apparatus and method to the respective deposit and extraction situation to locally assign an optimum degree of comminution to the rock formations present. Therefore, depending on the deposit, drilling into the ground can of course also be carried out vertically and/or horizontally and/or diagonally. Other drilling parameters or measured values may also be acquired to determine the rock-texture-dependent characteristic value as a measure for the grain size of the valuable mineral and for the purpose of setting an optimum degree of comminution of the rock.

What is claimed is:

1. A method for increasing the yield in a deposit comprising a rock which comprises at least one valuable mineral which is to be exposed as a result of the rock being comminuted, and at least one further mineral, the method comprising:
    performing a drilling operation using a drilling tool prior to the rock being extracted,
    acquiring at least one predefined drilling parameter for the drilling tool,
    acquiring at least one measured value characterizing a current drilling behavior of the drilling tool,
    performing a computational elimination of a dependency of the at least one measured value on the at least one drilling parameter, which provides at least one rock-texture-dependent characteristic value, and
    using the at least one rock-texture-dependent characteristic value as a measure for a grain size of the at least one valuable mineral in the rock and for setting a target degree of comminution for a comminution of the rock.

2. The method of claim 1, comprising comparing the at least one rock-texture-dependent characteristic value with predetermined characteristic values for the rock to which a specific grain size of the at least one valuable mineral and a target degree of comminution is assigned in each case, and
    wherein, in the event of a match of the at least one rock-texture-dependent characteristic value with one of the predetermined characteristic values, the grain size of the valuable mineral assigned thereto and the assigned target degree of comminution are also assigned to the at least one rock-texture-dependent characteristic value.

3. The method of claim 1, wherein the comminution of the rock exposes an ore mineral as the valuable mineral.

4. The method of claim 1, comprising:
    at a particular location, determining at least one of a depth of a drill bit of the drilling tool and position data concerning the position of the drilling tool in the deposit during the drilling operation,
    associating the at least one rock-texture-dependent characteristic value with the at least one of the drill bit depth and position data determined at the particular location, and
    during extraction of the rock at the particular location, using the at least one rock-texture-dependent characteristic value with the at least one of the drill bit depth and position data determined for the particular location for setting the degree of comminution for the extracted rock.

5. The method of claim 1, wherein the at least one drilling parameter is formed from at least one of:
    a pressure of a drill bit of the drilling tool,
    a rotational speed of the drill bit,
    a gas volume flow of a gas stream for removing drillings at the drill bit,
    an impact frequency of the drill bit,
    a previous period of use of the drill bit, and
    material or geometric data of the drill bit.

6. The method of claim 1, wherein the at least one measured value characterizing the current drilling behavior is selected from the group of measured values consisting of a drill speed, a resulting torque at a top drive of a drill bit, a gas pressure of a gas stream for removing drillings at the drill bit, an energy input into the drilling tool, and a vibration behavior of a drill pipe of the drilling tool.

7. The method of claim 1, wherein the at least one rock-texture-dependent characteristic value is also used for controlling at least one of (a) an extraction or blast operation, (b) a conveying operation, and (c) a material management operation in the region of the deposit.

8. The method of claim 1, wherein the target degree of comminution of the rock comprises an optimum degree of comminution of the rock.

9. An apparatus for increasing the yield in a deposit comprising a rock which comprises at least one valuable mineral which is to be exposed as a result of the rock being comminuted, and at least one further mineral, the apparatus comprising:
    at least one comminution machine configured to comminute the rock according to a controllable degree of comminution of the rock,
    at least one control unit configured to set a target degree of comminution at the at least one comminution machine,
    at least one drilling tool, at least one device configured to acquire at least one drilling parameter and at least one measured value, at least one computing unit programmed to perform a computational elimination of a dependency of the at least one measured value on the at least one drilling parameter to thereby determine at least one rock-texture-dependent characteristic value, at least one transmission device configured to transmit at least one manipulated variable, determined based on the determined at least one rock-texture-dependent characteristic value, to the at least one control unit, and the at least one control unit being configured to set the target degree of comminution at the at least one comminution machine based at least on the at least one manipulated variable received from the at least one transmission device.

10. The apparatus of claim 9, wherein the at least one transmission device corresponds to the at least one computing unit.

11. The apparatus of claim 9, wherein at least one device for acquiring the at least one measured value is provided on the at least one drilling tool in the form of at least one structure-borne noise sensor for detecting a vibration behavior of a drill pipe of the drilling tool.

12. The apparatus of claim 9, wherein the at least one computing unit is also configured to use the at least one rock-texture-dependent characteristic value for controlling at least one of an extraction or a blast operation, a conveying operation, and a material management operation in the region of the deposit.

13. The apparatus of claim 9, further comprising an extraction tool for the rock.

14. The apparatus of claim 13, wherein at least one of the drilling tool and the extraction tool comprises a GPS unit.

15. A method for processing a deposit of rock comprising at least one valuable mineral to be exposed by comminution of the rock, and at least one further mineral, the method comprising:

performing a drilling operation using a drilling tool, determining at least one predefined or controlled drilling parameter of the drilling tool, measuring at least one measured value characterizing as current drilling behavior of the drilling tool, determining a dependency of the at least one measured value on the at least one predefined or controlled drilling parameter of the drilling tool, calculating at least one rock-texture-dependent characteristic value from the at least one measured value based on the determined dependency of the at least one measured value on the at least one predefined or controlled drilling parameter of the drilling tool, and setting a target degree of comminution for a comminution of the rock based on the calculated at least one rock-texture-dependent characteristic value.

16. The method of claim 15, wherein calculating at least one rock-texture-dependent characteristic value comprises performing a computational elimination of the determined dependency of the at least one measured value on the at least one predefined or controlled drilling parameter of the drilling tool to determine the at least one rock-texture-dependent characteristic value.

* * * * *